United States Patent [19]

Merianos

[11] Patent Number: 4,952,704
[45] Date of Patent: Aug. 28, 1990

[54] BIS-(PYRROLIDONYL ALKYLENE) BIGUANIDES

[75] Inventor: John J. Merianos, Middletown, N.J.

[73] Assignee: GAF Chemicals Corporation, Wayne, N.J.

[21] Appl. No.: 350,882

[22] Filed: May 12, 1989

[51] Int. Cl.$^5$ ................. C01D 207/27; C07C 279/12; C07C 277/02
[52] U.S. Cl. ..................................... 548/519; 564/233
[58] Field of Search ..................... 548/519; 564/233

[56] References Cited

U.S. PATENT DOCUMENTS

| | | | |
|---|---|---|---|
| 3,468,898 | 9/1989 | Cutler et al. | 564/233 |
| 4,022,834 | 5/1977 | Gundersen | 564/233 |
| 4,567,174 | 6/1986 | Edwards et al. | 514/210 |
| 4,670,592 | 6/1987 | Eakin et al. | 544/86 |

Primary Examiner—Mukund J. Shah
Assistant Examiner—Edward C. Ward
Attorney, Agent, or Firm—Walter Katz; Marilyn J. Maue; Joshua J. Ward

[57] ABSTRACT

Antimicrobial bis-(pyrrolidonyl alkylene) biguanides having the formula:

A—Z—A where A is:

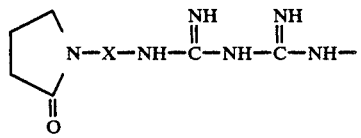

X is $C_2$-$C_4$ alkylene; and
Z is a bivalent bridging group, and acid addition salts thereof,
are provided herein.

12 Claims, No Drawings

BIS-(PYRROLIDONYL ALKYLENE) BIGUANIDES

BACKGROUND OF THE DISCLOSURE

1. Field of the Invention

This invention relates to bisbiguanide derivatives, and, more particularly to bis-(pyrrolidonyl alkylene) biguanide derivatives having antimicrobial activity.

2. Description of the Prior Art

Bisbiguanides are well known as antimicrobial agents. See, for example, U.S. Pat. Nos. 3,468,898; 4,022,834; 4,567,174; and 4,670,592. The bisbiguanide known as chlorhexidine, or, chemically, 1,6-bis(4-chlorophenyl-biguanido)-hexane, is a widely used antimicrobial compound; its formula is:

A—Z—A where A is:

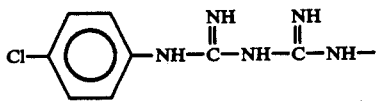

and Z is $-(CH_2)_6-$.

However, chlorhexidine is known to have many deficiencies, including: (1) the presence of a mutagenic p-chloroaniline moiety*; (2) low water solubility for the free base; (3) inactivity against bacterial spores at room temperature; (4) an antibacterial activity which is pH dependent in the range of pH 5-8, and which deteriorates at a pH below 5; and (5) incompatability in formulations containing surface active agents.

* (1) Scott, A. L. and Eccleston, E. "Investigation of the General Toxic and Heamatological Effects of para-chloroaniline in Several Species" *Proc. Env. Soc. Study of Drug Toxicity* Neutrotoxicity of Drugs 8, 195-204 (1966); and (2) Prasad, I, "Mutagenic Effects of the Herbicide 3',4'-Dichloropropionanilide and its Degradation Products", *Can. J. Microbiol* 16, 369-372 (1970).

Accordingly, it is an object of this invention to provide new and improved antimicrobial bis-biguanide derivatives.

A particular object of the invention is to provide novel antimicrobial biguanides having enhanced water solubility properties, low toxicity and better compatability with surfactants.

These and other objects and features of the present invention will be made apparent from the following particular description thereof.

DETAILED DESCRIPTION OF THE INVENTION

In accordance with the present invention, a bis-pyrrolidonyl moiety is introduced into bisbiguanides represented by chlorhexidine and other related compounds. The bis-pyrrolidonyl group in the bisbiguanide provides enhanced water solubility and decreased toxicity as compared to the p-chloroaniline moiety.

The bis-(pyrrolidonyl alkylene) biguanides of the invention have the following formula:

A—Z—A where
A is:

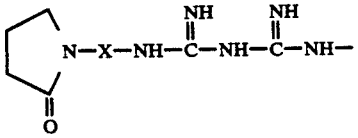

X is $C_2$–$C_4$ alkylene, e.g. ethylene, propylene and butylene;

Z is $C_2$–$C_{12}$ alkylene, which optionally may be interrupted, as by oxygen atoms, and also may incorporate cyclic nuclei which themselves may be saturated or unsaturated, and acid addition salts thereof.

The bridging group Z between the biguanides may be, for example, a trimethylene, hexamethylene, heptamethylene, octamethylene, nonamethylene, decamethylene, undecamethylene, dodecamethylene, tetradecamethylene or hexadecamethylene radical optionally interrupted with oxygen or sulfur. Suitable alkyl substituents on a straight chain alkylene radical Z are, for example, methyl, ethyl and n-propyl radicals, and a suitable value for Z in which two pairs of such alkyl radicals are joined together is, for example, the methylenebis(4-cyclohexyl) diradical.

Preferred values for Z are the hexamethylene, dodecamethylene, and bis-(2-ethoxy) ethane diradical.

The acid-addition salts of the invention may be derived from an inorganic or organic acid. In most circumstances it is preferred that the salts be derived from an acid which affords an anion which is suitable for human usage, for example, a pharmaceutically acceptable anion. Examples of such acids are hydrochloric, hydrobromic, phosphoric, sulphuric, acetic, D-gluconic, N-methyl-2-pyrrolidone-4-carboxylic, 2-pyrrolidone-5-carboxylic, methanesulphonic, carbonic, lactic and glutamic acids.

Particularly preferred compounds of the invention are 1,12-bis[1-(2-pyrrolidonylethyl)biguanido]dodecane; 1,6-bis[1-(2-pyrrolidonylethyl)biguanido]hexane; and 1,2-bis[1-(2-pyrrolidonylethyl)-5-(2-ethoxybiguanido)]ethane; and acid addition salts thereof.

The bis-(pyrrolidonyl alkylene) biguanide compounds of the invention may be prepared by a two-step synthesis. The first step comprises condensing sodium dicyanamide with the acid salt of a suitable diaminoalkane. The diamine provides the alkylene bridging group and the diamino group of the biguanide. Typical diamine starting materials include 1,6-diaminohexane, 1,12-diaminododecane and 1,2-bis(aminoethoxy) ethane. The intermediate product is a bis-cyanoguanidoalkane.

This condensation reaction generally is carried out in a solution of about 2 moles of the diamine di-hydrochloride and about 5 moles of the sodium dicyanamide. A suitable solvent, such as butanol, preferably is present in an amount of about 6–10 times the weight of solids employed in the reaction. The condensation is effected at reflux temperatues for about 4 hours. For 1,6-diaminohexane, for example, the reflux temperature is about 110° C. During the course of the reaction, a heavy precipitate of the bis-cyanoguanido compound is obtained. Filtration, washing with solvent and drying provides the intermediate in high yields, generally over 90% of theory, and of 95%–99% purity.

In the second step, the bis-cyanoguanido alkane intermediate is condensed with two moles of a suitable N-(2-aminoalkylene) pyrrolidone to form the desired bis-pyrrolidonyl-biguanide. This step also is preferably carried out in a solvent at reflux temperatures, for a suitable period of time.

The invention will now be illustrated by reference to the following examples.

A. Preparation of Bis-Cyanoguanidoalkane Intermediates

EXAMPLE 1

1,6-Bis-(Cyanoguanido) Hexane

A mixture of 40 g. (0.2 mole) of 1,6-diaminohexane dihydrochloride, 45 g. (0.5 mole) of sodium dicyanamide and 300 ml. of n-butanol solvent was heated at a reflux temperature of 110° C. for about 4 hours. Initially most of the solid dissolved, but soon a heavy precipitate was deposited. The reaction product then was filtered and the residue was suspended in water, stirred vigorously and filtered. The residue then was washed with water, and dried. The residue was 1,6-bis-(cyanoguanido) hexane. The yield was over 90% of theory, and was 95%-99% pure (m.p. 203°-205° C.).

EXAMPLE 2

1,12-Bis-Cyanoguanidododecane

The procedure of Example 1 was followed using 1,12-diaminododecane in place of 1,6-diaminohexane to provide the named intermediate compound, m.p. 245°-250° C.

EXAMPLE 3

1,2-Bis-(Cyanoguanidoethoxy)ethane 44 g. of 1,2-bis(2-aminoethoxy) ethane dihydrochloride (0.2 mole) and 45 g. of sodium dicyanamide (0.5 mole) and 300 ml. of n-butanol solvent were refluxed for about 4 hours. Then substantially all of the solvent was removed in a roto-evaporator, and the residue was dissolved in methanol.

Insoluble inorganic material then was separated from the reaction product by filtration, and the filtrate was treated with acetone until the product was precipitated. The yield was over 80% of theory, and of 95% purity, m.p. 160°-165° C.

B. Preparation of Bis-[{Pyrrolidonyl-alkylene)Biguanido]Alkane

EXAMPLE 4

1,6-Bis[1-(2-Pyrrolidonylethyl) biguanido]hexane:2HCl

A mixture of 25 g. (0.10 mole) of the 1,6-bis-(cyanoguanido) hexane intermediate of Example 1, 34.5 g. (0.21mole) of N-(2-aminoethyl) pyrrolidone and hydrochloride salt 200 ml. of n-butanol solvent was refluxed at 117° C. for 17 hours. The solvent then was removed by vacuum evaporation, and the residue was recrystallized from acetone. 54 g. (90% yield) of the named product was obtained.

EXAMPLE 5

1,12-Bis[1-(2-Pyrrolidonylethyl) biguanido]dodecane:2HCl

The procedure of Example 4 was followed using the intermediate of Example 2 to provide the named compound in similar yield and purity.

EXAMPLE 6

1,2-Bis[1-(2-pyrrolidonylethyl)-5-(2-Ethoxybiguanido)-]ethane:2HCl

A mixture of 28.2 g. (0.1 mole) of the 1,2-bis-(cyanoguanidoethoxy) ethane intermediate of Example 3, 36.2 g. (0.22 mole) of N-(2-aminoethyl)pyrrolidone hydrochloride salt and 200 g. of n-butanol was heated at a reflux temperature of 115° C. overnight. The solvent then was removed on a rotary evaporator. An equal volume of methanol was added to the residue and heated for dissolution. A precipitate was obtained from 10 times the volume of acetone. The solid product was dried at 1 mm. The yield was 63.5 g. (90%), m.p. 110°-125° C.

Properties of Compounds of Invention

EXAMPLE 7

Solubility in Water

The results in Table I below illustrates the water solubility of the free base and hydrochloride salts of the invention versus chlorhexidine. The solubility in water of the compounds of the invention is substantially greater than chlorhexidine.

TABLE 1

| | Form of Compound | |
| --- | --- | --- |
| Compound | Free Base (pH 8.5) | HCl Salt (pH 5.5) |
| Ex. 4 | 5% | 50% |
| Ex. 5 | 2% | 50% |
| Ex. 6 | 50% | 50% |
| Chlorhexidine | 0.008% | 1.8% |

EXAMPLE 8

Antibacterial Activity

The minimum inhibitory concentrations (MIC) against different Gram positive and Gram negative microorganisms, and fungi, were determined and the results are shown in Table 2 below.

TABLE 2

| | Minimum Inhibitory Concentration (ppm) | | | | |
| --- | --- | --- | --- | --- | --- |
| | Gram Negative Microorg. | | Gram Positive Microorg. | | |
| Compound | E. Coli | Ps. aer. | Strept. py. | Staph. aur. | Fungi |
| Ex. 4 | 250 | 250 | ≦50 | ≦100 | 100 |
| Ex. 5 | 250 | >500 | ≦50 | ≦50 | ≦50 |
| Ex. 6 | 100 | ≦100 | ≦50 | >500 | ≦50 |
| Chlorhexidine gluconate | 5 | 50 | 5 | 2.5 | >200 |

The results show that the compounds of the invention have effective antimicrobial and fungistat activity.

What is claimed is:

1. Antimicrobial bis-(pyrrolidonyl alkylene) biguanides having the formula:

$$A—Z—A$$

where
A is:

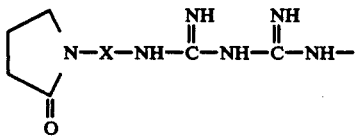

X is a C₂ alkylene group, and

Z is a hexamethylene, dodecamethylene or bis-(2-ethoxy) ethane bridging group, and acid addition salts thereof.

2. A compound according to claim 1 wherein Z is $-(CH_2)_6-$.

3. A compound according to claim 1 wherein Z is $-(CH_2)_{12}-$.

4. A compound according to claim 1 wherein said acid addition salt is derived from an inorganic or organic acid selected from hydrochloric, hydrobromic, phosphoric, sulfuric, acetic, d-gluconic, 2-pyrrolidone-5-carboxylic, methanesulfonic, carbonic, lactic, glutamic and N-methyl-2-pyrrolidone-4-carboxylic acids.

5. A compound according to claim 1 which is 1,12-bis[1-(2-pyrrolidonylethyl)biguanido]dodecane, and acid addition salts thereof.

6. A compound according to claim 1 which is 1,6-bis[1-(2-pyrrolidonylethyl)biguanido]hexane, and acid addition salts thereof.

7. A compound according to claim 1 which is 1,2-bis[1-(2-pyrrolidonylethyl)-5-(2-ethoxybiguanido)]ethane and acid addition salts thereof.

8. A process of making a compound of claim 1 which comprises condensing a bis(cyanoguanido) alkane or bis(cyanoguanido) alkoxyalkane with an aminoalkylene pyrrolidone.

9. A process according to claim 8 wherein 1,6-bis(cyanoguanido) hexane is condensed with aminoethyl pyrrolidone to form 1,6-bis[1-(2-pyrrolidonylethyl)-biguanido]hexane.

10. A process according to claim 8 wherein 1,12-bis(cyanoguanido) hexane is condensed with aminoethyl pyrrolidone to form 1,12-bis[1-(2-pyrrolidonylethyl)-biguanido]dodecane.

11. A process according to claim 8 wherein bis-(cyanoguanidoethoxy) ethane is condensed with aminoethyl pyrrolidone to form 1,2-bis[1-(2-pyrrolidonylethyl)-5-(2-ethoxybiguanido)]ethane.

12. A process according to claim 11 wherein said bis-(cyanoguanidoethoxy)ethane is prepared by reacting an acid salt of 1,2-bis(2-aminoethyl)ethane and sodium dicyanamide.

* * * * *